United States Patent
Dai et al.

(10) Patent No.: US 6,986,649 B2
(45) Date of Patent: Jan. 17, 2006

(54) MICROPUMP WITH INTEGRATED PRESSURE SENSOR

(75) Inventors: Xunhu Dai, Gilbert, AZ (US); Chenggang Xie, Phoenix, AZ (US)

(73) Assignee: Motorola, Inc., Schaumburg, IL (US)

( * ) Notice: Subject to any disclaimer, the term of this patent is extended or adjusted under 35 U.S.C. 154(b) by 402 days.

(21) Appl. No.: 10/411,031

(22) Filed: Apr. 9, 2003

(65) Prior Publication Data
US 2004/0202548 A1    Oct. 14, 2004

(51) Int. Cl.
*F04B 43/04*    (2006.01)

(52) U.S. Cl. .................... 417/413.2; 417/559; 417/566

(58) Field of Classification Search ............ 417/413.2, 417/413.3, 559, 566
See application file for complete search history.

(56) References Cited

U.S. PATENT DOCUMENTS

| | | | |
|---|---|---|---|
| 5,798,641 A * | 8/1998 | Spagna et al. | 324/228 |
| 6,422,823 B2 * | 7/2002 | Bernard et al. | 417/18 |
| 6,531,341 B1 * | 3/2003 | Peterson et al. | 438/123 |
| 6,655,923 B1 * | 12/2003 | Lisec et al. | 417/92 |
| 6,732,589 B2 * | 5/2004 | Eickhoff et al. | 73/715 |
| 6,782,755 B2 * | 8/2004 | Tai et al. | 73/754 |
| 2003/0002995 A1 * | 1/2003 | Urano et al. | 417/322 |
| 2004/0037718 A1 * | 2/2004 | Xie et al. | 417/413.2 |

* cited by examiner

Primary Examiner—Timothy S. Thorpe
Assistant Examiner—Ryan Gillan

(57) ABSTRACT

An exemplary system and method for manufacturing micropump systems having integrated piezoresistive sensors is disclosed as including inter alia: a substrate, an inlet channel, an outlet channel, a pumping cavity, a first valve for permitting fluid flow from the inlet channel to the pumping cavity and restricting backflow of purged fluid from the pumping cavity to the inlet channel; a second valve for permitting fluid flow from the pumping cavity to an outlet channel and restricting backflow of purged fluid from the outlet channel to the pumping cavity; a pump actuator element; a pressure sensing cavity surface capable of at least partial mechanical deformation; a plurality of piezoresistors disposed within the sensing cavity; a plurality of contact pads; a plurality of conductive pathways connecting the piezoresistors and the contact pads; and a substantially monolithic device package, wherein the sensing cavity is substantially contained within the micropump device package. Disclosed features and specifications may be variously controlled, adapted or otherwise optionally modified to improve micropump operation in any microfluidic application. Exemplary embodiments of the present invention representatively provide for piezoresistive pressure sensors that may be readily integrated with existing portable ceramic technologies for the improvement of device package form factors, weights and other manufacturing and/or device performance metrics.

23 Claims, 1 Drawing Sheet

US 6,986,649 B2

MICROPUMP WITH INTEGRATED PRESSURE SENSOR

FIELD OF INVENTION

The present invention relates to micropumps, and more particularly, in one representative and exemplary embodiment, to multilayer ceramic micropumps having integrated piezoresistive pressure sensors for improved performance, efficiency and fabrication cost savings in microfluidic applications.

BACKGROUND

Development of microfluidic technology has generally been driven by parallel ontological advancements in the commercial electronics industry with the ever-increasing demand for sophisticated devices having reduced part counts, weights, form factors and power consumption while improving or otherwise maintaining overall device performance. In particular, advancement of microfluidic technology has met with some success in the areas of packaging and the development of novel architectures directed to achieving many of these aims at relatively low fabrication cost.

The development of microfluidic systems, based on for example, multilayer laminate substrates with highly integrated functionality, have been of particular interest. Monolithic substrates formed from laminated ceramic have been generally shown to provide structures that are relatively inert or otherwise stable to most chemical reactions as well as tolerant to high temperatures. Additionally, monolithic substrates typically provide for miniaturization of device components, thereby improving circuit and/or fluidic channel integration density. Potential applications for integrated microfluidic devices include, for example, fluidic management of a variety of microsystems for life science and portable fuel cell applications. One representative application includes the use of ceramic materials to form microchannels and/or cavities within a laminate structure to define, for example, a high aspect ratio micropump.

Conventional pumps and pumping designs have been used in several applications; however, many of these are generally too cumbersome and complex for application with microfluidic systems. For example, existing designs typically employ numerous discrete components externally assembled or otherwise connected together with plumbing and/or component hardware to produce ad hoc pumping systems. Consequently, conventional designs have generally not been regarded as suitable for integration with portable ceramic technologies or in various applications requiring, for example, reduced form factor, weight or other desired performance and/or fabrication process metrics. Moreover, previous attempts with integrating microfluidic pumps in laminated substrates have met with considerable difficulties in producing reliable fluidic connections and/or hermetic seals capable of withstanding manufacturing processes and/or operational stress while maintaining or otherwise reducing production costs. Accordingly, despite the efforts of prior art pump designs to miniaturize and more densely integrate components for use in microfluidic systems, there remains a need for high aspect ratio micropumps having integrated pressure sensors suitably adapted for incorporation with, for example, a monolithic device package.

SUMMARY OF THE INVENTION

In various representative aspects, the present invention provides a system and method for fluid transport and pressure sensing in microfluidic systems. A representative design is disclosed as comprising a fluid inlet opening, a fluid outlet opening, a pumping cavity, a reservoir cavity, a check valve substantially enclosed within each of the cavities, means for moving fluid through the device, and an integrated piezoresistive pressure sensing component. An high aspect ratio micropump, in accordance with one embodiment of the present invention, may be formed utilizing multilayer ceramic technology in which check valves and a piezoresistive pressure sensor are integrated into a laminated ceramic structure; however, the disclosed system and method may be readily and more generally adapted for use in any fluid transport system. For example, the present invention may embody a device and/or method for providing integrated pumping and/or valving systems for use in fuel cell fuel delivery and/or partitioning applications.

One representative advantage of the present invention would allow for improved process control and manufacturing of integrated micropump systems at substantially lower cost. Additional advantages of the present invention will be set forth in the Detailed Description which follows and may be obvious from the Detailed Description or may be learned by practice of exemplary embodiments of the invention. Still other advantages of the invention may be realized by means of any of the instrumentalities, methods or combinations particularly pointed out in the claims.

BRIEF DESCRIPTION OF THE DRAWINGS

Representative elements, operational features, applications and/or advantages of the present invention reside inter alia in the details of construction and operation as more fully hereafter depicted, described and claimed—reference being made to the accompanying drawings forming a part hereof, wherein like numerals refer to like parts throughout. Other elements, operational features, applications and/or advantages will become apparent to skilled artisans in light of certain exemplary embodiments recited in the detailed description, wherein:

Figure 1:
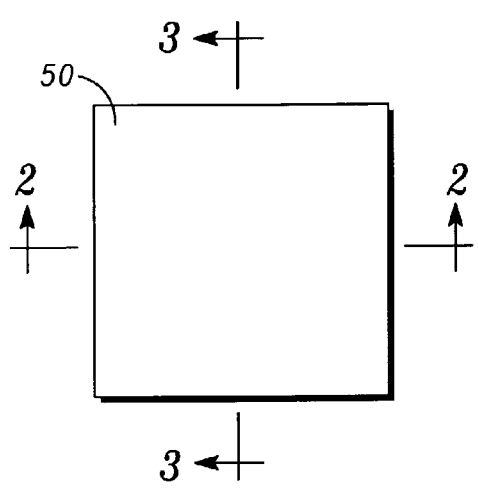
FIG. 1 representatively depicts a top plan view of a pressure sensor device package in accordance with an exemplary embodiment of the present invention.

Those skilled in the art will appreciate that elements in the Figures are illustrated for simplicity and clarity and have not necessarily been drawn to scale. For example, the dimensions of some of the elements in the Figures may be exaggerated relative to other elements to help improve understanding of various embodiments of the present invention. Furthermore, the terms 'first', 'second', and the like herein, if any, are used inter alia for distinguishing between similar elements and not necessarily for describing a sequential or chronological order. Moreover, the terms 'front', 'back', 'top', 'bottom', 'over', 'under', and the like in the Description and/or in the claims, if any, are generally employed for descriptive purposes and not necessarily for comprehensively describing exclusive relative position. Skilled artisans will therefore understand that any of the preceding terms so used may be interchanged under appropriate circumstances such that various embodiments of the invention described herein, for example, are capable of operation in other orientations than those explicitly illustrated or otherwise described.

DETAILED DESCRIPTION OF EXEMPLARY EMBODIMENTS

The following descriptions are of exemplary embodiments of the invention and the inventors' conceptions of the best mode and are not intended to limit the scope, applicability or configuration of the invention in any way. Rather, the following description is intended to provide convenient illustrations for implementing various embodiments of the invention. As will become apparent, changes may be made in the function and/or arrangement of any of the elements described in the disclosed exemplary embodiments without departing from the spirit and scope of the invention.

Various representative implementations of the present invention may be applied to any system and/or method for fluid transport. As used herein, the terms "fluid", "fluidic" and/or any contextual, variational or combinative referent thereof, are generally intended to include anything that may be regarded as at least being susceptible to characterization as generally referring to a gas, a liquid, a plasma and/or any matter, substance or combination of compounds substantially not in a solid or otherwise effectively immobile condensed phase. As used herein, the terms "inlet" and "outlet" are generally not used interchangeably. For example, "inlet" may generally be understood to comprise any cross-sectional area or component feature of a device, the flux through which tends to translate fluid from a volume element substantially external to the device to a volume element substantially internal to the device; whereas "outlet" may be generally understood as referring to any cross-sectional area or component feature of a device, the flux through which tends to translate fluid from a volume element substantially internal to the device to a volume element substantially external to the device. On the other hand, as used herein, the terms "liquid" and "gas" may generally be used interchangeably and may also be understood to comprise, in generic application, any fluid and/or any translationally mobile phase of matter. As used herein, the term "purged", as well as any contextual or combinative referent or variant thereof, is generally intended to include any method, technique or process for moving a volume element of fluid through the outlet of a device so as to dispose or otherwise positionally locate the "purged" volume element external to the device. Additionally, as used herein, the terms "valve" and "valving", as well as any contextual or combinative referents or variants thereof, are generally intended to include any method, technique, process, apparatus, device and/or system suitably adapted to control, affect or otherwise parameterize fluid flow scalar quantities (e.g., volume, density, viscosity, pressure, etc.) and/or fluid flow vector quantities (i.e., flow direction, velocity, acceleration, jerk, etc.). Additionally, as used herein, the terms "pump" and "pumping", or any contextual or combinative referents or variants thereof, are generally intended to include any method, technique, process, apparatus, device and/or system suitably adapted to flow or otherwise translate a fluid volume element from a first location to a second location.

A detailed description of an exemplary application, namely a system and method for making a micropump integrated with a piezoresistive sensing element in a laminar device package is provided as a specific enabling disclosure that may be readily generalized by skilled artisans to any application of the disclosed system and method for microfluidic transport and integrated pressure sensing in accordance with various embodiments of the present invention. Moreover, skilled artisans will appreciate that the principles of the present invention may be employed to ascertain and/or realize any number of other benefits associated with fluid transport such as, but not limited to: improvement of pumping efficiency; reduction of device weight; reduction of device form factor; improved sample loading in microfluidic assays; improvement in sample throughput; sample multiplexing and/or parallel sample processing; integration with micro-array techniques and/or systems; microfluidic sample transport; pumping of fuel and/or fuel components in a fuel cell system and/or device; and any other applications now known or hereafter developed or otherwise described in the art.

In one representative application, in accordance with an exemplary embodiment of the present invention, a pressure sensing component, as generally depicted, for example, in FIGS. 1–5, is disclosed. The device package 50 generally includes: a plurality of piezoresistors 130, 150 disposed within a sensing cavity; a plurality of contact pads 140, 200, 300; a plurality of conductive pathways 110, 210 communicably connecting piezoresistors 130, 150 with contact pads 140, 200, 300. The sensing cavity is substantially internally disposed within the device package. Another exemplary embodiment of the present invention describes a novel fabrication method for manufacturing piezoresistive pressure sensor devices in multilayer ceramic (MLC) structures with low temperature cofired ceramic (LTCC) technologies.

In one exemplary embodiment, in accordance with various representative aspects of the present invention, piezoresistors 130, 150 may comprise at least one sensing piezoresistor 130 disposed near a sensing area of the sensing cavity. A sensing area may include any surface or any portion of a surface capable of at least partial mechanical deflection or deformation so as to mechanically actuate the resistance value of a sensing piezoresistor 130 in correspondence to the mechanical deflection or deformation of the sensing area. The device may also include reference piezoresistors 150 disposed effectively displaced, set away or otherwise positionally removed from the sensing area of the sensing cavity such that mechanical deformation of the sensing area does not effectively actuate the resistance of the reference piezoresistor 150.

For example, a cavity with single layer of tape ceramic provided as sensing membrane may be formed in a multilayer ceramic structure using inter alia DuPont 951 GreenTape™ (available from DuPont Microcircuit Materials, E. I. Du Pont de Nemours and Company, 14 T. W. Alexander Drive, Research Triangle Park, N.C., USA), as representatively depicted in FIG. 2. Cofireable piezoresistive pastes such as, for example, 3414 series (available from Electro-Science Lab, 416 East Church Road, King of Prussia, Pa. 19406-2625, USA) may be used to form sensing resistors on the sensing membrane and reference resistors away from the sensing cavity. Discrete piezoresistive components may also be alternatively, conjunctively and/or sequentially employed.

Pressure or load sensing may be achieved through a resistor layout employing, for example, a Wheatstone bridge configuration. Operational tests have demonstrated pressure sensitivities on the order of about 1.3 mV/kPa for 1.6 mil thick ceramic membrane over a 200 mil square cavity.

Figure 2:
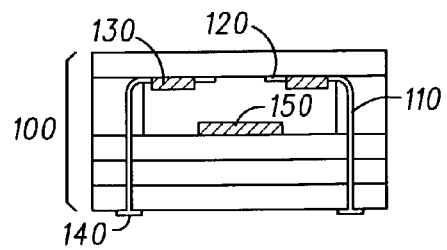
FIG. 2 representatively illustrates a cross-section, side view of the sensor device package generally depicted in FIG. 1 along the '2—2' axis.
Figure 3:
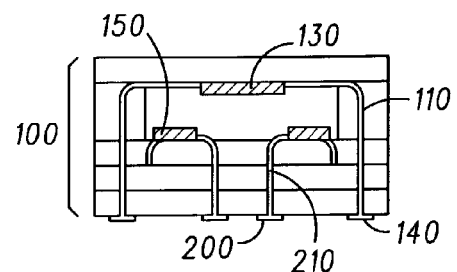
FIG. 3 representatively illustrates a cross-section, side view of the sensor device package generally depicted in FIG. 1 along the '3—3' axis.
Figure 4:
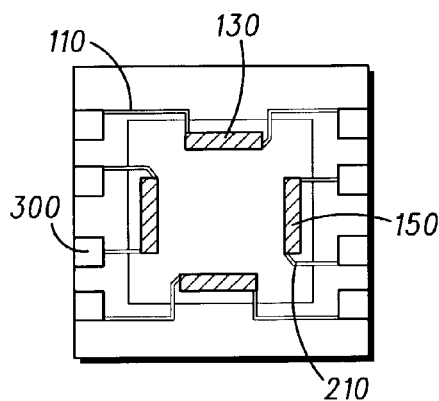
FIG. 4 representatively illustrates a cross-section, plan view of the sensor device package generally depicted in FIG. 1.
Figure 5:
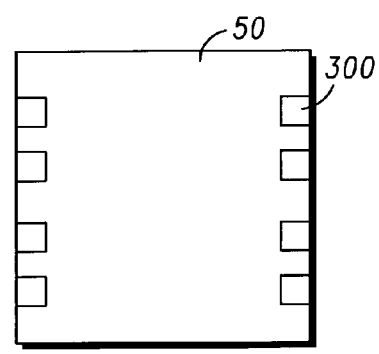
FIG. 5 representatively illustrates a bottom plan view of the sensor device package generally depicted in FIG. 1.

Sensing resistors 130 may be disposed on a sensing membrane surface while reference resistors 150 may be positioned on a generally mechanically inactive surface of the sensing cavity, as generally depicted, for example, in FIGS. 2 and 3. Conductor pathways 110, 210 may be externally accessed, for example, by typical multi-layer ceramic interconnection to surface I/Os.

In one exemplary embodiment, the utilization of cofireable piezoresistive paste and LTCC tape dielectric to form piezoresistors inside MLC cavity would substantially reduce packaging cost. Moreover, the sensing unit could be easily integrated with other multi-layer ceramic functionalities to form multi-layer 100 based microsystems. Additionally, reference resistors 150 may be cofired onto the bottom of the sensing cavity, thus permitting a similar interface for all resistors inter alia to minimize the effect of resistance from piezoresistor/LTCC interaction.

Figure 6:
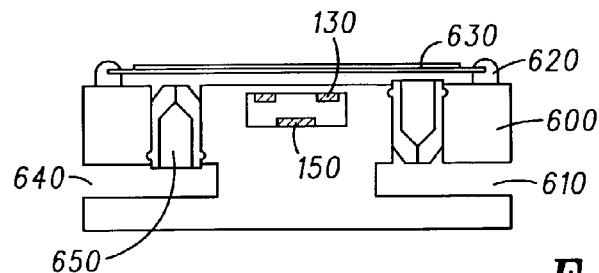
FIG. 6 representatively depicts a cross-section, elevation view of an assembled and substantially sealed micropump device package in accordance with another embodiment of the present invention.

In one representative application, in accordance with an exemplary embodiment of the present invention, a laminar micropump system, as generally depicted in FIG. 6, is disclosed. The system generally includes at least one substantially flexible, or otherwise at least partially deformable, material comprising, for example, a duck-bill valve 650. The disclosed valving system, in certain representative embodiments, may include features to control the effective magnitude of cross-sectional area presented for fluid acceptance in order to at least partially control or otherwise parameterize fluid flux through inlet opening 640 and/or outlet opening 610. For example, inlet opening 640 and/or outlet opening 610 may comprise a taper, a flare, a constriction, a plurality of corrugations, a bend, a pinch, an oblique plane of fluid acceptance (e.g., wherein inlet opening 640 and/or outlet opening 610 facial alignment generally may be other than normal to the instantaneous vector of fluid flow) or such other means, features and/or methods now known, subsequently developed or otherwise hereafter described in the art.

The operation of valves 650 generally provide passive means for substantially preventing or otherwise controlling or restricting the backflow of purged outlet fluid into a reservoir chamber and/or the pumping chamber generally disposed underneath piezo-membrane 630. For example, the outlet valve generally permits fluid flow when the flow vector (e.g., the direction of fluid pressure; also termed the "fluid transport gradient") corresponds to translation of fluid volume elements away from inlet opening 640 through fluidic channels toward outlet opening 610. Additionally, the outlet valve, in accordance with representative aspects of the present invention, conjunctively provides for effective prevention of fluid flow to outlet opening 610 when the instantaneous fluid transport gradient corresponds to translation of fluid volume elements away from outlet opening 610 through fluidic channels toward inlet opening 640 (e.g., "backflow"). In an alternative exemplary embodiment, a reservoir chamber and/or pumping chamber may further or alternatively comprise a mixing chamber, a reaction chamber and/or a fuel reformer chamber (in the case of application of the present invention, for example, to fuel cell systems).

One exemplary implementation of the present invention may be manufactured from a substrate, wherein a laminar substrate is provided for the fabrication of a piezo-driven micropump with an integrated piezoresistive pressure sensor. Outlet opening 610 is suitably configured to provide a path for fluid transport to the pumping chamber. Fluidic channels generally provide fluidic communication between the pumping chamber and an external reservoir chamber. The reservoir chamber may be generally configured to provide effective fluidic communication to outlet opening 610. Skilled artisans, however, will appreciate that other channel configurations and/or circuit geometries may be employed in order to define inter alia various fluidic transport paths, for example, in a laminar substrate in accordance with various other embodiments of the present invention.

In one representative embodiment, openings for disposing valves 650 are defined in the device package substrate such that valves 650 may be suitably deposited in the pumping chamber and/or a reservoir chamber respectively, from substantially the same surface of the substrate presented during fabrication. One exemplary benefit of the disclosed method of same-side device assembly resides in fewer process fabrication/control steps resulting in substantially lowered cost of production.

Other means for providing substantially passive valving function other than that of a duck-bill valve include, for example: a slit, a flapper valve, a plunger, a shuttle, a rotary stop-cock, a one-way flow gate or any other device feature, method or means for substantially passive valving now known, subsequently developed or hereafter described in the art. The same may be alternatively, conjunctively or sequentially employed in various embodiments of the present invention. Skilled artisans will appreciate that the term "passive", as it may refer to valving devices and/or function, generally connotes the ability of a valve and/or valve device feature so characterized, to actuate the operation of restriction, constriction and/or dilation of fluid inlet acceptance and/or fluid outlet purging in effective correspondence to the forces nominally inherent to the translation of fluid volume elements through the valve device. That is to say, when the fluid flow is in a first direction, the fluidic forces operate to actuate the valve into a first conformation (i.e., substantially open); and, when the fluid flow is in a second direction (e.g., for a binary valve, generally given as the "opposite direction"), the fluidic forces operate to actuate the valve into a second conformation (i.e., substantially closed).

In various exemplary embodiments, valves 650 may be fabricated from silicone, silicone-based rubber, rubber, metal, metal alloy, polymer or such other materials whether now known or subsequently discovered or otherwise hereafter described in the art. In an exemplary application where passive check valves 650 comprise flapper valves, the valves may comprise a silicone-based rubber material. Additionally, valves 650 may optionally comprise means for attachment, such as, for example, an extension tab having a substantially annular retaining ring for securing or otherwise at least partially immobilizing valve 650 within the device package substrate. Various other attachment means and/or packaging features for retaining, localizing or otherwise disposing check valves known in the art may be used as well. For example, the following retaining means may be conjunctively, alternatively or sequentially employed: adhesives, organic epoxies, a mechanical anchor, press-fit clips, solder, clamps, seals, adaptors and/or such other retention, connection or attachment devices, means and/or methods, whether now known or otherwise hereafter described in the art.

FIG. 6 further depicts two passive valves 650 disposed within an exemplary monolithic package substrate with pump actuator element 630. In one representative embodiment, pump actuator may comprise a piezoelectric micropump element 630. In an exemplary embodiment, piezoelectric element 630 may be secured to the package substrate by, for example, solder 620. Accordingly, the substrate may comprise solder-wettable features that are generally provided to permit secure solder attachment of piezoelectric element 630 and/or a cover to the substrate. Various other means for attaching piezoelectric element 630 and/or a cover to the package substrate may include, for example: epoxy, adhesive and/or such other attachment means and/or methods whether now known or hereafter described in the art. In yet another exemplary embodiment of the present invention, piezoelectric element 630 may alternatively be integrated within the package substrate; for example, between ceramic layers in a position substantially internal to the device as the package is built up. As describe vide supra sensing resistors 130 may be disposed on a sensing membrane surface while reference resistors 150 may be positioned on a generally mechanically inactive surface of an integrated sensing cavity, as generally depicted, for example, in FIGS. 6, 2 and 3. Conductor pathways 110, 210 may be externally accessed, for example, by typical multi-layer ceramic interconnection to surface I/Os.

As electric current is supplied to the package, piezoelectric element 630 operates as a deformable diaphragm membrane whose deformation (e.g., "stroke volume") causes oscillating over- and under-pressures in the pumping chamber. The pumping chamber, in an exemplary embodiment, may be bounded by, for example, two passive check valves 650. The pump actuation mechanism 630 need not be limited to piezoelectric actuation, but may alternatively, sequentially or conjunctively be driven by electrostatic or thermopneumatic actuation or such other means and/or methods now known, subsequently derived or otherwise hereafter described in the art.

During the movement of the diaphragm element (i.e., piezoelectric element 630) in a direction which tends to enlarge the pump chamber volume, an under-pressure is generated in the pump chamber causing fluid to flow through inlet channel 640 in a flow direction which causes the pump inlet valve to distend toward piezoelectric element 630 thereby permitting fluid to flow around the inlet valve to enter into the pump chamber. Since the fluid transport gradient during the under-pressure stroke is anti-parallel to the fluid flow acceptance conformation of the outlet valve, the outlet valve seals so as to at least partial reduce the occurrence of fluid disposed in outlet channel 610 re-entering via fluidic communication into the pump chamber (e.g., backflow). Accordingly, this component of the pump cycle is termed the "supply mode" or the "supply stroke".

In the alternate and next phase of the stroke cycle, the movement of the diaphragm element 630 in a direction which tends to reduce the pump chamber volume causes an over-pressure to be generated in the pump chamber, thereby flowing fluid through outlet opening 610 as a result of fluid flowing out of the pumping chamber in a flow direction which causes the outlet valve to distend thereby permitting fluid to flow around the outlet valve to outlet channel 610. Since the fluid transport gradient during the over-pressure stroke is anti-parallel to the fluid flow acceptance conformation of the inlet valve, the inlet valve seals so as to at least partial reduce the occurrence of fluid disposed in the pump chamber from back-flowing into the inlet channel 640. Accordingly, this component of the pump cycle is termed the "pumping mode" or the "delivery stroke".

The volume of the pump chamber upon relaxation of the actuation diaphragm is known as the dead volume $V_0$ and the volume the actuation membrane deflects during a pump cycle generally defines the stroke volume $\Delta V$. The ratio between the stroke volume and dead volume may be used to express the compression ratio $\epsilon$. Due in part to the relatively small stroke of micro-actuators and the relatively large dead volume, the compression ratio $$\varepsilon = \frac{\Delta V}{V_0}$$

is usually relatively small.

The pressure cycles (e.g., "pressure waves") generated from the actuation supply and pump modes typically operate to switch the valves. In the limit of the pump chamber being filled with an ideally incompressible fluid, the pressure waves would ideally propagate from the actuation diaphragm to the valves with no net pressure loss—in which case, the compression ratio is generally not regarded as an important metric of pump performance and/or efficiency. However, where the fluid medium is not ideally incompressible, there exists a compressibility factor $\kappa>0$ which may be employed to characterize the tendency of a real fluid to dampen the propagation of the actuation pressure wave $\Delta p$. If the pressure change $\Delta p$ falls below a certain value $p'$ (e.g., the threshold pressure differential for actuation of a valve), the pump generally will not properly operate. Accordingly, a minimum condition for operation of any micropump may be expressed as $|\Delta p| \geq |p'|$.

Given the compressibility $\kappa$ of a liquid, the pressure change $\Delta p$ may be calculated (if the volume change $\Delta V$ induced by the actuator is known) in accordance with the equation $V_0 + \Delta V = V_0(1 - \kappa \Delta p)$. If this expression is substituted into those previously presented, the compressibility ratio $\epsilon$ for liquid micropumps may be expressed as $\epsilon_{liquid} \geq \kappa |p'|$. Accordingly, a threshold valve actuation pressure $p'$ of 1 kPa in combination with the compression ratio for water $\kappa_{water}$ ($5*10^{-9}$ m$^2$/N) would yield a minimum compression ratio $\epsilon_{water}$ of $5*10^{-6}$. In this case, where the stroke volume $\Delta V$ is assumed to be 50 nl, the dead volume $V_0$ generally may not exceed 10 ml. Skilled artisans, however, will appreciate that the preceding example will generally only hold true where the pump chamber is completely filled with liquid and no degassing and/or bubble occlusion occurs during micropump operation and therefore provides a first-order approximation for the determination of operational parameters and/or design specifications.

In the case of a gas pump, assuming an ideal gas having an adiabatic coefficient of $\gamma$ (1.4 for air), at atmospheric pressure $p_0$ and an actuation pressure wave of magnitude $\Delta p$, the following expression may be obtained:

$$p_0 V_0^\gamma = (p_0 + \Delta p)(V_0 + \Delta V)^\gamma$$

Accordingly, it may be shown that the criterion for the compression ratio of a gas micropump may be similarly derived as $$\varepsilon_{gas} \geq \left( \frac{p_0}{p_0 - |p'|} \right)^{\frac{1}{\gamma}} - 1$$

and, in the case of isothermal state transitions, the adiabatic coefficient γ may be taken as equal to unity. For the device previously presented for the micropumping of water (e.g., p'=1 kPa and ΔV=50 nl), the dead volume $V_0$ for the same system adapted for the micropumping of air must generally not exceed 5 μl.

In conventional micropump operation, gas bubbles may often remain in the pump chamber during the priming procedure and/or the liquid may even volatized in response to temperature changes during operation. In these cases, the expression for the compression ratio of a liquid $\epsilon_{liquid} \geq \kappa |p'|$ will no longer hold true since the compressibility of the gas bubble is generally much larger than the compressibility of the liquid. Depending on the volume of the gas bubble, the actuation pressure wave will be dampened in an amount that may be calculated if the volume of the gas bubble is substituted for the dead volume in the appropriate equation presented vide supra. If the gas bubble volume becomes so large that the actuation pressure wave falls below the threshold valve actuation pressure, the micropump will fail. Consequently, in the limit of the entire pump chamber volume being filled with a gas, the operational design criteria for liquid self-priming pumps converges to the design criteria for those of gas micropumps.

Additionally, in practical applications, the design criteria may even need to be more stringent to account for higher-order fluid dynamics. For example, self-priming liquid micropumps must typically suck the liquid meniscus from the inlet 640 into the pump chamber, thereby increasing the threshold critical pressure p' in parity with the surface tension of the meniscus at the juncture between and/or within, for example, the microfluidic channels and the microfluidic valves. Those skilled in the art will recognize that other fluid dynamics and/or parametric contributions may require consideration in the determination of optimal operational specifications for a micropump in accordance with the present invention as they may be employed in a variety of practical applications and/or operating environments. The same shall be regarded as within the scope and ambit of the present invention.

In one exemplary application, in accordance with a representative embodiment of the present invention, a multilayer ceramic (MLC) based micro pump is disclosed as comprising integrated piezoresistive pressure sensor(s) to monitor real-time pressure changes within the pumping chamber utilizing, for example, low temperature cofired ceramic (LTCC) technologies. A pressure sensing cavity may be fabricated with single layer of tape ceramic as a sensing membrane in an MLC structure using for example DuPont 951 GreenTape. The pressure sensing cavity may also be integrated into a MLC based micropump substrate with the sensing membrane comprising a part of the pumping chamber. This technique may generally provide real time pressure measurement in the pump chamber which could be used, for example, to adjust the actuation for controlled fluid management and may be particularly attractive for development of highly integrated MLC based Microsystems. Potential applications include low cost sensors for harsh environment/chemicals and integrated fluidic sensing in micro-channel devices.

Exploitation of the cofireability of piezoresistive paste and LTCC tape dielectric to form piezoresistors inside MLC cavity would effectively eliminate or otherwise reduce overall packaging cost. In another exemplary application, a pressure measurement may be obtained from an outlet region of an integrated device (down stream) to provide feedback to an actuation control system.

In the foregoing specification, the invention has been described with reference to specific exemplary embodiments; however, it will be appreciated that various modifications and changes may be made without departing from the scope of the present invention as set forth in the claims below. The specification and figures are to be regarded in an illustrative manner, rather than a restrictive one and all such modifications are intended to be included within the scope of the present invention. Accordingly, the scope of the invention should be determined by the claims appended hereto and their legal equivalents rather than by merely the examples described above. For example, the steps recited in any method or process claims may be executed in any order and are not limited to the specific order presented in the claims. Additionally, the components and/or elements recited in any apparatus claims may be assembled or otherwise operationally configured in a variety of permutations to produce substantially the same result as the present invention and are accordingly not limited to the specific configuration recited in the claims.

Benefits, other advantages and solutions to problems have been described above with regard to particular embodiments; however, any benefit, advantage, solution to problems or any element that may cause any particular benefit, advantage or solution to occur or to become more pronounced are not to be construed as critical, required or essential features or components of any or all the claims.

As used herein, the terms "comprises", "comprising", or any variation thereof, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present invention, in addition to those not specifically recited, may be varied or otherwise particularly adapted by those skilled in the art to specific environments, manufacturing specifications, design parameters or other operating requirements without departing from the general principles of the same.

We claim:

1. A method for making a micropump device, comprising:
   providing a substrate, said substrate comprising a first surface and fluidic channels;
   said fluidic channels comprising an inlet channel, an outlet channel and a pumping cavity;
   said inlet channel suitably adapted to receive fluid for transport through said micropump device;
   said outlet channel suitably adapted to purge fluid from said micropump device;
   providing a first valve for effectively permitting flow of fluid from said inlet channel to said pumping cavity, said first valve effectively restricting backflow of purged fluid from said pumping cavity to said inlet, and said first valve deposited through a first opening on said first surface of said substrate;
   providing a second valve for effectively permitting flow of fluid from said pumping cavity to said outlet channel, said second valve effectively restricting backflow of purged fluid from said outlet channel to said pumping cavity, and said second valve deposited through a second opening on said first surface of said substrate;
   effectively disposing a pump actuator over said first opening;

effectively disposing a cover over said second opening;
providing a sensing cavity having at least one surface;
providing a sensing area disposed on at least a portion of at least one sensing cavity surface, wherein said sensing area is capable of at least partial mechanical deformation;
providing a plurality of piezoresistors disposed within said sensing cavity;
providing a plurality of contact pads;
providing a plurality of conductive pathways communicably connecting said piezoresistors and said contact pads;
providing a substantially monolithic device package, wherein said sensing cavity is substantially internally disposed within said micropump device package; and
disposing said sensing area substantially near said pump chamber such that mechanical deformation of said sensing area at least partially corresponds to fluid pressure in the region of said pump chamber;
disposing at least one sensing piezoresistor near said sensing area of said sensing cavity such that mechanical deformation of said sensing area effectively actuates the resistance of said sensing piezoresistor; and
disposing at least one reference piezoresistor effectively removed from said sensing area of said sensing cavity such that mechanical deformation of said sensing area does not substantially actuate the resistance of said reference piezoresistor.

2. The method of claim 1, wherein said first opening and said second opening comprise the same opening and said pump actuator comprises the cover.

3. The method of claim 1, wherein said first valve and said second valve comprise at least one of a passive valve, a check valve, a passive check valve, a duck-bill valve and a flapper valve.

4. The method of claim 3, wherein said first valve and said second valve comprise at least one of silicone, silicone-based rubber, rubber, metal, metal alloy and polymer.

5. The method of claim 1, wherein said pump actuator comprises a piezoelectric membrane element.

6. The method of claim 1, further comprising the step of aligning said plurality of piezoresistors as substantially orthogonal pairs.

7. The method of claim 1, further comprising the step of sealing said sensing cavity in order to provide a substantially hermetic seal.

8. The method of claim 1, further comprising the step of disposing said contact pads on a substantially exterior surface of said monolithic device package.

9. The method of claim 1, wherein said ceramic monolithic device package is built up from a plurality of ceramic tape layers.

10. The method of claim 9, wherein the resulting multilayer ceramic structure comprises a low temperature cofired ceramic (LTCC).

11. The method of claim 1, further comprising the step of providing a Wheatstone bridge configuration of conductive connection between said piezoresistors and said contact pads.

12. A microfluidic pumping device manufactured in accordance with the method of claim 1, wherein said pump actuator comprises a piezoelectric actuator.

13. The microfluidic pumping device of claim 12, further comprising means for retaining at least one of said first valve and said second valve within a microfluidic channel.

14. The microfluidic pumping device of claim 13, wherein said retaining means comprises at least one of a substantially annular retaining ring, a valve anchor and a seal.

15. The microfluidic pumping device of claim 12, wherein said piezoelectric actuator comprises at least one of a unimorphic piezoelectric membrane element and a bimorphic piezoelectric membrane element.

16. The device of claim 12, wherein the device package comprises at least one of ceramic, glass, a polymer material, metal and a metal alloy.

17. The device of claim 12, further comprising at least one of ceramic tape and DuPont 951 GreenTape.

18. A microfluidic pumping system comprising a plurality of micropump devices manufactured in accordance with the method of claim 1, wherein said plurality of micropumps are in common fluidic communication.

19. The microfluidic pumping system of claim 18, wherein said common fluidic communication of said micropumps comprises at least one of a series configuration and a parallel configuration.

20. A method for making a micropump device, comprising:
providing a substrate, said substrate comprising a first surface and fluidic channels;
said fluidic channels comprising an inlet channel, an outlet channel and a pumping cavity;
said inlet channel suitably adapted to receive fluid for transport through said micropump device;
said outlet channel suitably adapted to purge fluid from said micropump device;
providing a first valve for effectively permitting flow of fluid from said inlet channel to said pumping cavity, said first valve effectively restricting backflow of purged fluid from said pumping cavity to said inlet, and said first valve deposited through a first opening on said first surface of said substrate;
providing a second valve for effectively permitting flow of fluid from said pumping cavity to said outlet channel, said second valve effectively restricting backflow of purged fluid from said outlet channel to said pumping cavity, and said second valve deposited through a second opening on said first surface of said substrate;
effectively disposing a pump actuator over said first opening;
effectively disposing a cover over said second opening;
providing a sensing cavity having at least one surface;
providing a sensing area disposed on at least a portion of at least one sensing cavity surface, wherein said sensing area is capable of at least partial mechanical deformation;
providing a plurality of piezoresistors disposed within said sensing cavity;
providing a plurality of contact pads;
providing a plurality of conductive pathways communicably connecting said piezoresistors and said contact pads;
providing a substantially monolithic device package, wherein said sensing cavity is substantially internally disposed within said micropump device package; and
enclosing said sensing cavity with a layer of ceramic tape.

21. The method of claim 20, further comprising the step of providing means for retaining at least one of said first valve and said second valve within a microfluidic channel.

22. The method of claim 21, wherein said retaining means comprises at least one of a substantially annular retaining ring, a valve anchor and a seal.

23. The method of claim 20, wherein at least one of said pump actuator and said cover are soldered to said first surface of said substrate.

* * * * *